US005594007A

United States Patent [19]
Chenard

[11] Patent Number: 5,594,007
[45] Date of Patent: Jan. 14, 1997

[54] METHOD FOR TREATING SPINAL CORD TRAUMA WITH PHENOLIC 2-PIPERIDINO-1-ALKANOLS

[75] Inventor: Bertrand L. Chenard, Waterford, Conn.

[73] Assignee: Pfizer Inc., New York, N.Y.

[21] Appl. No.: 195,797

[22] Filed: Feb. 14, 1994

Related U.S. Application Data

[63] Continuation-in-part of Ser. No. 119,122, Sep. 16, 1993, Pat. No. 5,455,250, which is a continuation of Ser. No. 687,273, Apr. 18, 1991, abandoned.

[51] Int. Cl.$^6$ .................. A61K 31/445; A61K 31/40; A61K 31/05
[52] U.S. Cl. .................. 514/315; 514/327; 514/408; 514/731
[58] Field of Search ...................... 514/315, 327, 514/408, 731, 810, 879, 884

[56] References Cited

U.S. PATENT DOCUMENTS

| | | | |
|---|---|---|---|
| 4,902,695 | 2/1990 | Ornstein | 514/307 |
| 4,968,678 | 11/1990 | Ornstein | 514/222.2 |
| 5,163,313 | 11/1992 | Haas, Jr. et al. | 73/41 |
| 5,185,343 | 2/1993 | Chenard | 514/278 |
| 5,192,751 | 3/1993 | Thor | 514/82 |
| 5,272,160 | 12/1993 | Chenard | 514/327 |
| 5,338,754 | 8/1994 | Chenard | 514/422 |
| 5,352,683 | 10/1994 | Mayer et al. | 514/289 |
| 5,455,250 | 10/1995 | Chenard | 514/305 |

FOREIGN PATENT DOCUMENTS

| | | |
|---|---|---|
| 0441506 | 8/1991 | European Pat. Off. . |
| WO9014088 | 11/1990 | WIPO . |
| WO9014087 | 11/1990 | WIPO . |
| WO9117156 | 11/1991 | WIPO . |

OTHER PUBLICATIONS

Schoepp et al., J. Neur. Trans., 85, 131–43 (1991).
Lehman, Drugs of the Future, 14(11), 1059 (1989).
McLachlan, Canadian Journal of Neurological Science, 19(4), 487 (1992).
Trujillo and Akil, Science, 251, 85 (1991).
Lehman et al., PIPS, 11, 1 (1990).
Bundagard et al., J. Med. Chem., 32, 2503–07 (1989).
Hansen and Krogsgaard–Larson, Med. Res. Rev., 10, 55–94 (1990).
Murphy et al., British J. Pharmacology, 95, 932–38 (1988).
Harrison and Simmonds, British J. Pharmacology, 84, 381–91 (1984).

*Primary Examiner*—Kevin E. Weddington
*Attorney, Agent, or Firm*—Peter C. Richardson; Gregg C. Benson; Robert T. Ronau

[57] ABSTRACT

A method of blocking N-methyl-D-aspartic acid (NMDA) receptor sites in a mammal in need thereof with an effective NMDA blocking (neuroprotective and antiischemic) amount of prodrug esters of 2-piperidino-1-alkanol derivatives and prodrug esters of 2-azabicyclo-1-alkanol derivatives and analogs and pharmaceutically acceptable salts thereof; methods of using these compounds in the treatment of stroke, spinal cord trauma, traumatic brain injury, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised.

1 Claim, No Drawings

METHOD FOR TREATING SPINAL CORD TRAUMA WITH PHENOLIC 2-PIPERIDINO-1-ALKANOLS

CROSS-REFERENCE TO RELATED APPLICATIONS

This application is a continuation-in-part of U.S. application Ser. No. 08/119,122, filed Sep. 16, 1993, now U.S. Pat. No. 5,455,250, which is the U.S. national stage of International application no. PCT/US92/02131, having an international filing date of Mar. 24, 1992, which is a continuation of U.S. application Ser. No. 07/687,273, filed Apr. 18, 1991, now abandoned.

BACKGROUND OF THE INVENTION

The present invention is directed to prodrug esters of phenolic 2-piperidino-1-alkanols, as depicted by the formulas (I) and (II), below; to pharmaceutical compositions thereof; to a method of treating stroke, traumatic head injury, or a CNS degenerative disease therewith; and to ketone intermediates of the formulas (III) and (IV), below, which are useful in their synthesis.

The phenolic compounds from which the present compounds derive are disclosed in U.S. Pat. Nos. 5,185,343 and 5,272,160, both of which are hereby incorporated by reference. These phenolic compounds are of the formulas

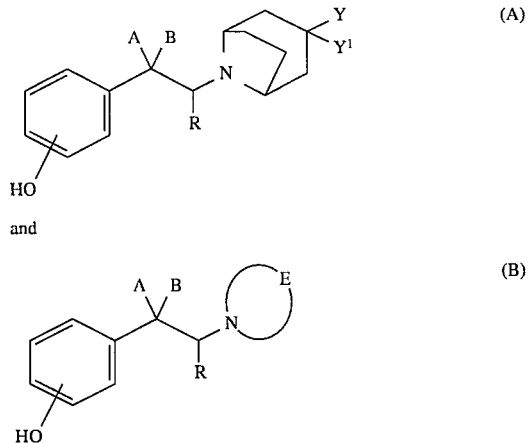

wherein A and B are taken separately and A is hydrogen and B is hydroxy, or A and B are taken together and are oxygen (forming a carbonyl group); and the groups R, E, Y and $Y^1$ are as defined below for the corresponding ester derivatives of the formulas (I), (II), (III) and (IV).

The compounds of the formulas (A) and (B) wherein the groups A and B are taken separately to form a 1-alkanol, like the present compounds of the formulas (I) and (II), generally possess selective antiischemic and excitatory amino acid receptor blocking activity (i.e., a neuroprotective effect) in good measure, while at the same time they have lowered or no significant hypotensive effect.

The excitatory amino acids are an important group of neurotransmitters that mediate excitatory neurotransmission in the central nervous system. Glutamic acid and aspartic acid are two endogenous ligands that activate excitatory amino acid (EAA) receptors. There are two types of EAA receptors, ionotropic and metabotropic, which differ in their mode of signal transduction. There are at least three distinct ionotropic EAA receptors characterized by the selective agonist that activates each type: the NMDA, (N-methyl-D-aspartic acid), the AMPA (2-amino-3-(5-methyl-3-hydroxy-isoxazol-4-yl)propanoic acid), and the kainic acid receptors. The ionotropic EAA receptors are linked to ion channels that are permeable to sodium and, in the case of NMDA receptors, calcium. Metabotropic receptors, linked to phosphoinositide-hydrolysis by a membrane associated G-protein, are activated by quisqualic acid, ibotenic acid, and (1S,3R)-1-aminocyclopentane 1,3-dicarboxylic acid.

The NMDA receptor is a macromolecular complex consisting of a number of distinct binding sites that gate on ion channel permeable to sodium and calcium ions. Hansen and Krogsgaard-Larson, Med. Res. Rev., 10, 55–94 (1990). There are binding sites for glutamic acid, glycine, and polyamines, and a site inside the ion channel where compounds such as phencyclidine (PCP) exert their antagonist effects. Competitive NMDA antagonists are compounds which block the NMDA receptor by interacting with the glutamate binding site. The ability of a particular compound to competitively bind to the NMDA glutamate receptor may be determined using a radioligand binding assay. See Murphy et al., British J. Pharmacol. 95, 932–938 (1988). The antagonists may be distinguished from the agonists using a rat cortical wedge assay. See Harrison and Simmonds, British J. Pharmacol., 84, 381–391 (1984). Examples of competitive NMDA antagonists include D-2 amino 5-phosphonopentanoic acid (D-AP5), and D-2-amino-7-phosphonoheptanoic acid, Schoepp et al., J. Neur. Transm., 85, 131–143 (1991).

Antagonists of neurotransmission at NMDA receptors are useful therapeutic agents for the treatment of neurological disorders. U.S. Pat No. 4,902,695 is directed to series of competitive NMDA antagonists useful for the treatment of neurological disorders, including epilepsy, stroke, anxiety, cerebral ischemia, muscular spasms, and neurodegenerative disorders such as Alzheimer's disease and Huntington's disease. U.S. Pat. No. 4,968,878 is directed to a second series of competitive NMDA receptor antagonists useful for the treatment of similar neurological disorders and neurodegenerative disorders. U.S. Pat. No. 5,192,751 provides a method of treating urinary incontinence in a mammal which comprises administering an effective amount of a competitive NMDA antagonist.

NMDA antagonists are also useful therapeutic agents with anticonvulsant, anxiolytic, muscle relaxant, and antipsychotic activity. J. Lehman, The NMDA Receptor, Drugs of the Future, 14, No. 11, p. 1059 (1989). NMDA antagonists have also been reported to be effective for treating migraine (Canadian Journal of Neurological Science, 19(4), p. 487 (1992)); drug addiction (Science, 251, p. 85 (1991)); and neuro-psychotic disorders related to AIDS (PIPS, 11, p. 1 (1990).

Ifenprodil, a racemic, so-called dl-erythro compound having the relative stereochemical formula

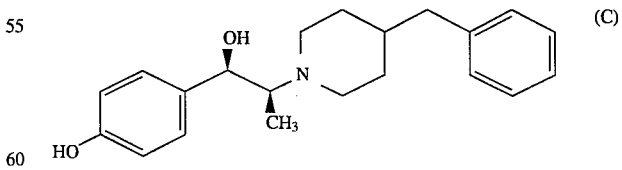

has been shown to possess antiischemic and excitory aminoacid receptor blocking activity; Gotti et al., J. Pharm. Exp. Therap., v. 247, pp. 1211–21 (1988); Carter et al., loc. cit., pp. 1222–32 (1988). See also French Patent 2546166. However, in ifenprodil, this activity is not selective. Indeed ifenprodil is marketed as a hypotensive agent, a utility shared by a number of close analogs; Carron et al., U.S. Pat.

No. 3,509,164; Carron et al., Drug Res., v. 21, pp. 1992–1999 (1971).

So-called prodrug esters, which in general enhance oral absorption and are hydrolyzed in vivo to form the active component of the ester, have become quite common in the medicinal art. For example, Bundgaard et ed., J. Med. Chem., v. 32, pp. 2503–7 (1989) have described certain prodrug esters of the type

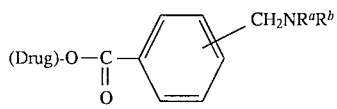

wherein $R^a$ and $R^b$ are taken separately, $R^a$ is hydrogen or lower alkyl, and $R^b$ is lower alkyl; or $R^a$ and $R^b$ are taken together with the nitrogen to which they are attached to form, for example, a morpholine or 4-methylpiperazine ring.

SUMMARY OF THE INVENTION

The present invention is directed to a method of blocking N-methyl-D-aspartic acid (NMDA) receptor sites in a mammal in need of said blocking comprising administering to said mammal an effective amount of a racemic or optically active compound of the formula

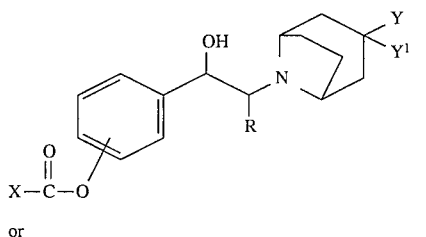

or

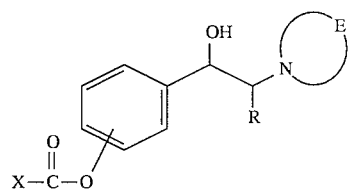

wherein

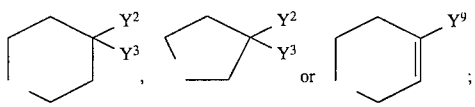

R is H, $(C_1-C_6)$alkyl, $(C_2-C_6)$alkenyl or $(C_2-C_6)$alkynyl;
X is phenyl, benzyl, $(C_1-C_3)$alkoxy, phenoxy or one of said groups substituted on aromatic carbon by

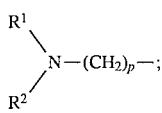

5 p is 1 or 2;
$R^1$ and $R^2$ are taken separately and are each independently hydrogen or $(C_1-C_6)$alkyl, or $R^1$ and $R^2$ are taken together with the nitrogen to which they are attached to form a pyrrolidine, piperidine or morpholine ring, or one of said rings substituted by $(C_1-C_3)$alkyl;

when either Y and $Y^1$ or $Y^2$ and $Y^3$ are taken together, they are

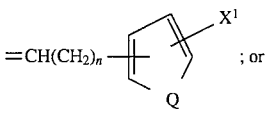

when either Y and $Y^1$ are taken separately, Y is H or OH, and $Y^1$ is

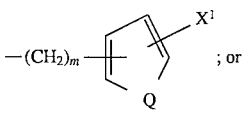

Y is hydrogen and $Y^1$ is

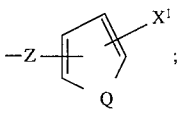

when $Y^2$ and $Y^3$ are taken separately, and $Y^2$ is OH and $Y^3$ is

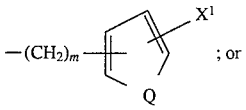

$Y^9$ is

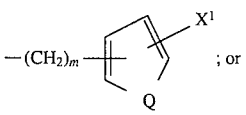

n is 0, 1, 2 or 3;
m is 0, 1, 2, 3 or 4;
Q is S or CH=CH;
$X^1$ is hydrogen, $(C_1-C_3)$alkyl, $(C_1-C_3)$alkoxy or halo; and
Z is O, S, SO or $SO_2$; or
a pharmaceutically acceptable acid addition salt thereof.
Said acid addition salts include, but are not limited to, those formed with such acids as HCl, $H_2SO_4$, $H_3PO_4$, $HNO_3$, $CH_3SO_3H$, p-$CH_3C_6H_4SO_3H$, acetic acid, maleic acid and citric acid.

The present invention is further directed to methods of treating stroke, spinal cord trauma, multiinfarct dementia, CNS degenerative diseases such as Alzheimer's disease, senile dementia of the Alzheimer's type, Huntington's disease, Parkinson's disease, epilepsy, amyotrophic lateral sclerosis, pain, AIDS dementia, psychotic conditions, drug addictions, migraine, hypoglycemia, anxiolytic conditions, urinary incontinence and an ischemic event arising from CNS surgery, open heart surgery or any procedure during which the function of the cardiovascular system is compromised with a compound of the formula (I) hereinabove or a pharmaceutically acceptable salt thereof.

The most preferred method of use of the compounds of formula (I) or a pharmaceutically acceptable salt thereof is directed to the treatment of migraine.

The preferred compounds are racemic or optically active compounds wherein R is methyl and have 1S*,2S* relative stereochemistry:

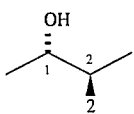

alternatively and equivalently depicted as:

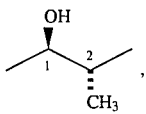

and referred to as 1R*,2R* relative stereochemistry. See Rigaudy et ed., eds., IUPAC Nomenclature of Organic Chemistry, 1979 Edition, Pergamon Press, New York, 1979, p. 482. Preferred values of X are phenyl, p-(dimethylaminomethyl)phenyl, p-(diethylaminomethyl)-phenyl, m-(diethylaminomethyl)phenyl, p-(piperidino-methyl)phenyl, p-(2-methylpiperidinomethyl)phenyl and p-(morpholinomethyl)phenyl. The preferred position of the XCOO group on the benzene ring is para to the 1-hydroxyalkyl substituent.

DETAILED DESCRIPTION OF THE INVENTION

The present invention is readily carried out. According to the preferred route, the compounds of the above formula (I) and (II) are formed by conventional hydride reduction of a corresponding, already acylated ketone of the formula (III) or (IV).

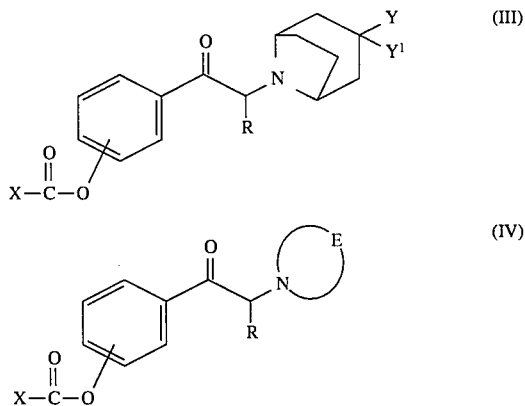

Hydride reducing agents generally useful in this reduction include lithium aluminum hydride and sodium borohydride. Generally an excess of the hydride reducing agent is employed, but to avoid reduction of the ester group, lithium aluminum hydride is employed at low temperature, e.g., at −50 C to −100 C, conveniently about −78 C, the temperature of a dry ice-acetone bath. In any event, the hydride reduction is carded out in a reaction-inert solvent, such as tetrahydrofuran in the case of lithium aluminum hydride and absolute ethanol in the case of sodium borohydride. With sodium borohydride temperature is less critical, with temperatures in the range of 0–30 C being generally preferred.

As used in the preceding paragraph, and elsewhere herein, the expression "reaction inert solvent" refers to any solvent which does not interact with starting materials, reagents, intermediates or products in a manner which adversely affects the yield of the desired product.

Further according to the preferred method of preparing the present compounds of the above formulas (I) and (II), the acylated ketone precursors of the above formulas (III) and (IV) are obtained by acylation of a known ketone derivative, respectively, of the formulas (A) and (B), above, wherein A and B are taken together to form a carbonyl group. Said acylation is readily accomplished by a number of conventional methods which are well known in the organic chemical art. When the ketone (A) or (B) contains a tertiary aliphatic alcohol group (which is the case when either Y or $Y^2$ is hydroxy), this acylation is necessarily selective, but still, in general, is readily accomplished because of the greater activity of the phenolic group relative to the hindered tertiary, alcoholic group. The preferred methods borrow from coupling methods used in the synthesis of peptides. According to one of the preferred methods, a substantially molar equivalent of the acid is coupled with the phenolic ketone by the action of substantially one molar equivalent of 1-ethyl-3-(3-dimethylaminopropyl)-carbodiimide. This coupling is generally carried out in a reaction-inert solvent such as methylene chloride in the presence of 10–20% molar excess of a tertiary amine such as 4-dimethylaminopyridine. Temperature is not critical, with temperatures in the range of 0–50 C being generally satisfactory, and ambient temperatures (generally about 17–27 C) preferred, since the cost of heating or cooling is avoided.

Alternatively, the compounds of the formulas (I) and (II) are obtained directly by acylation of the appropriate, known phenolic 1-alkanol compound of the above formulas (A) and (B) wherein A and B are taken separately, A is hydrogen and B is hydroxy. Indeed, when the 1-alkanol is already available in resolved form, this is a preferred route to the optically active forms of the present esters.

The ketonic and 1-alkanol precursors of the formulas (A) and (B) depicted above are disclosed in U.S. Pat. Nos. 5,185,343 and 5,272,160 cited above. In the ketones of that reference wherein the phenol group is protected, the protecting group is removed by the same methods there particularly disclosed for the deprotection of phenol-protected 1-alkanol derivatives. Such a deprotection method is also specifically described in Preparations detailed below.

The present compounds of the formula (I), (II) and (III) possess selective neuroprotective activity, based upon their antiischemic activity and ability to block excitory aminoacid receptors, while at the same time having lowered or no significant hypotensive activity. The antiischemic activity of the present compounds is determined according to one or more of the methods which have been detailed previously by Gotti et al. and Carter et al. cited above, or by similar methods. The ability of the compounds of the present invention to block excitatory amino acid receptors is demonstrated by their ability to block N-methyl-D-aspartic acid-induced (NMDA) elevations of cGMP in neonatal rat cerebellums according to the following procedure. Cerebellums from ten 8–14 day old Wistar rats are quickly excised and placed in 4 C. Krebs/bicarbonate buffer, pH 7.4 and then chopped in 0.5 mm×0.5 mm sections using a McIlvain tissue chopper (The Nickle Laboratory Engineering Co., Gomshall, Surrey, England). The resulting pieces of cerebellum are transferred to 100 ml of Krebs/bicarbonate buffer at 37° C. which is continuously equilibrated with 95:50 $O_2/CO_2$. The pieces of cerebellum are incubated in such a manner for ninety minutes with three changes of the buffer. The buffer then is decanted, the tissue centrifuged (1 min., 3200 r.p.m.) and the tissue resuspended in 20 ml of the Krebs/bicarbonate buffer. Then, 250 ml aliquots (approximately 2 mg) are removed and placed in 1.5 ml microfuge tubes. To those tubes are added 10 ml of the compound under study from a stock solution followed, after a 10 minute incubation period, by 10 ml of a 2.5 mM solution of NMDA to start the reaction. The final NMDA concentration is 100 mM. Controls do not have NMDA added. The tubes are incubated for one minute at 37° C. in a shaking water bath and then 750 ml of a 50 mM Tris-Cl, 5 mM EDTA solution is added to stop the reaction. The tubes are placed immediately in a boiling water bath for five minutes. The contents of each tube then are sonicated for 15 seconds using a probe sonicator set at power level three. Ten microliters are removed and the protein determined by the method of Lowry, Anal. Biochem. 100:201–220 (1979). The tubes are then centrifuged (5 min., 10,000×g), 100 ml of the supernatant is removed and the level of cyclic GMP (cGMP) is assayed using a New England Nuclear (Boston, Mass.) cGMP RIA assay according to the method of the supplier. The data is reported as pmole cGMP generated per mg. protein. Undesired hypotensive activity is also determined by known methods, for example, according to the methods of Canon et al., also cited above.

The present prodrug esters are dosed at weight levels which are chemically equivalent to the weight levels of the fully active phenolic forms, as detailed in my published International application WO 90/14088 cited above. For example, for a 10 mg dose of a phenol having a molecular weight of 327, the amount of a prodrug ester having a molecular weight of 516 will be (10 mg×516)/327=15.8 mg.

The present prodrug esters are formulated into oral and parenteral dosage forms according to the same conventional methods which are used in the formulation of the corresponding phenols as described in U.S. Pat. Nos. 5,185,343 and 5,272,160.

The present invention is illustrated by the following examples, but is not limited to the details thereof.

All non-aqueous reactions were run under nitrogen for convenience and generally to maximize yields. All solvents/diluents were dried according to standard published procedures or purchased in a predried form. All reactions were stirred either magnetically or mechanically. NMR specta are recorded at 300 MHz and are reported in ppm. The NMR solvent was $CDCl_3$ unless other specified.

EXAMPLE 1

2-(4-Hydroxy-4-phenylpiperidino)-1-(4-(4-(morpholinomethyl)benzoyloxy)phenyl-1-propanone To a mixture of 4-(morpholinomethyl)benzoic acid (3.17 g, 12.3 mmol), 1-(4-hydroxyphenyl)-2-(4-hydroxy-4-phenylpiperidino)-1-propanone(4.0 g, 12.29 mmol), and 1-ethyl-3-(3-dimethylaminopropyl)-carbodiimide hydrochloride (2.36 g, 12.31 mmol) in methylene chloride (75 mL) was added 4-dimethylaminopyridine (1.88 g, 15.39 mmol). The heterogeneous mixture was allowed to stir overnight under a nitrogen atmosphere at ambient temperature. The mixture was washed with saturated aqueous bicarbonate (2×50 mL), dried by filtration through phase separating filter paper, and concentrated to a glassy yellow solid. Trituration with ether and hexane yielded 5.17 g, 80% of a light yellow solid product which was suitable for further reaction without additional purification. A sample recrystallized from ethyl acetate/hexane had: m.p. 126–126.5 C; NMR ($CDCl_3$) 8.22 (d, J=8.6 Hz, 2H), 8.13 (d, J=7.8 Hz, 2H), 7.47 (t, J=7.3 Hz, 4H), 7.34–7.19 (m, 5H), 4.13 (q, J=6.6 Hz, 1H), 3.70 (t, J=4.4 Hz, 4H), 3.57 (s, 2H), 2.97–2.79 (m, 2H), 2.67–2.60 (m, 2H), 2.44 (t, J=4.5 Hz, 4H), 2.18–1.98 (m, 2H), 1.78–1.67 (m, 3H), 1.31 (d, J=6.6 Hz, 3H). IR (KBr) 3270, 2960, 2942, 2912, 2830, 2821, 1743, 1682, 1596, 1390, 1273, 1199.

Analysis calculated for $C_{32}H_{36}N_2O_5$: C, 72.70; H, 6.86; N, 5.30. Found: C, 72.42; H, 6.65; N, 5.25.

In like manner, other phenol-ketones of the Preparation below are converted to:

2-(4-Benzyl-4-hydroxypiperidino )-1-(4-(4-morpholinomethyl)benzoyloxy)phenyl)-1-propanone; and 2-(4-(4-Chlorophenyl)-4-hydroxypiperidino)-1-(4-(morpholinomethyl)benzoyloxy)phenyl-1-propanone.

EXAMPLE 2

Racemic (1S_*,2S_*)- and (1R_*,2S_*)-2-(4-Hydroxy-4-phenylpiperidino)-1-(4-(4-(morpholinomethyl)benzoyloxy)phenyl)-1-propanol Sodium borohydride (0.39 g, 10.3 mmol) was partially dissolved in absolute ethanol (25 mL) and chilled to 0 C and an ice cold ethanol solution (50 mL) of the title ketone product of the preceding Example (5.0 g, 9.46 mmol) was added over 2 minutes. The reaction was stirred at 0 C overnight, and then it was quenched with glacial acetic acid (6 mL). The volatiles were distilled from the reaction mixture under vacuum while maintaining the pot temperature at or below 0 C. The residual material was flash chromatographed on silica gel (2×6 inches, ethyl acetate/hexane gradient elution). No product was obtained. Continued elution with a methanol/ethyl acetate gradient gave 2.90 g of the (S_*,S_*)-title product, which was recrystallized from ethanol to give 1.8 g of purified (S_*,S_*)-title product: m.p. 172–173 C; NMR ($CDCl_3$) 8.17 (d, J=8.3 Hz, 2H), 7.56–7.25 (m, 9H), 7.20 (d, J=8.5 Hz, 2H), 4.33 (d, J=9.7 Hz, 1H), 3.73 (t, J=4.6 Hz, 4H), 3.59 (s, 2H), 3.11 (dt, J=1.7, 11.6 Hz, 1H), 2.76–2.59 (m, 4H), 2.47 (t, J=4.5 Hz, 4H), 2.31–2.07 (m, 3H), 1.85 (br d, J=13.2 Hz, 3H), 0.89 (d, J=6.7 Hz, 3H); IR (KBr) 3452, 3245, 2970, 2930, 2893, 1730, 1273, 1262, 1194, 1114, 1075, 797, 758.

Analysis calculated for $C_{32}H_{38}N_2O_5$: C, 72.43; H, 7.22; N, 5.28. Found: C, 72.58; H, 6.95; N, 5.26.

Continued gradient elution with methanol/ethyl acetate gave 1.71 g of the (R_*,S_*)-title product as its acetate salt. It was further purified by recrystallization from ethanol/ether to give purified (R_* ,S_*)-title product, 0.60 g of white powder: m.p. 164–165 C; NMR (DMSO-$d_6$) 8.10 (d, J=8.2 Hz, 2H), 7.54 (d, J=8.2 Hz, 2H), 7.45 (t, J=7.4 Hz, 4H), 7.31 (t, J=7.5 Hz, 2H), 7.21 (d, J=8.3 Hz, 3H), 5.82 (br s, 4H), 4.91 (d, J=4.1 Hz, 1H), 3.59 (t, J=4.6 Hz, 4H), 3.01–2.71 (m, 6H), 2.50 (m, 4H), 2.20–1.80 (m with s at 1.90 ppm, 5H), 1.64–1.60 (m, 2H), 1.01 (d, J=6.6 Hz, 3H). IR (KBr) 2961, 2856, 2820, 1733, 1268, 1201, 1071.

Analysis calculated for $C_{32}H_{38}N_2O_5 \cdot C_2H_4O_2$: C, 69.13; H, 7.17; N, 4.74. Found: C, 70.39; H, 6.85; N, 4.86.

By the same method, the additional products of the preceding Example are converted to:

(1S_*,2S_*)- and (1R_*,2S_*)-2-(4-Benzyl -4-hydroxypiperidino)-1-(4-(4-(morpholinomethyl)benzoyloxy)-phenyl-1-propanol; and (1S_*,2S_*)- and (1R_*,2S_*)-2-(4-(4-Chlorophenyl)-4-hydroxypiperidino)-1-(4-(4-(morpholinomethyl)benzoyl-oxy)phenyl-1-propanol.

EXAMPLE 3

1-(4-(4-Diethylaminomethyl)benzoyloxy)phenyl)
-2-(4-hydroxy-4-phenylpiperidino )-1-propanone The coupling of 4-diethylaminomethylbenzoic acid with 1-(4-hydroxyphenyl)-2-(4-hydroxy-4-phenylpiperidino)-1-propanone was carried out essentially as in Example 1. The crude product was treated with ether and hexane with stirring and yielded the creamy white product in 73% yield in a state of purity suitable for the reduction step. A sample recrystallized from ether/hexane gave a white powder which had: m.p. 106–107 C; NMR (CDCl$_3$) 8.25 (d, J=8.8 Hz, 2H), 8.15 (d, J=8.3 Hz, 2H), 7.51 (t, J=7.2 Hz, 4H), 7.38–7.22 (m, 5H), 4.16 (q, J=6.7 Hz, 1H), 3.66 (s, 2H), 2.96–2.81 (m, 2H), 2.71–2.67 (m, 2H), 2.55 (q, J=7.1 Hz, 4H), 2.22–2.00 (m, 3H), 1.82–1.69 (m, 2H), 1.35 (d, J=6.7 Hz, 3H), 1.07 (t, J=7.1 Hz, 6H). IR(KBr) 3452, 2969, 2935, 2833, 1738, 1681, 1264, 1198, 1164, 1064.

Analysis calculated for C$_{32}$H$_{38}$N$_2$O$_4$: C, 74.68; H, 7.44; N, 5.44. Found: C, 74.34; H, 7.28; N, 5.49.

In like manner, other phenol-ketones of the Preparation below are converted to:

1-(4-(4-(Diethylaminomethyl)benzoyloxy)phenyl) -2(3-(phenylthio)-8-azabicyclo[3.2.1]oct-8-yl)-1-propanone;

2-(3-(4-Chlorophenylthio)-8-azabicyclo[3.2.1]oct -8-yl)-1-(4-(4-diethylaminomethyl)benzoyloxy)phenyl)-1-propanone;

1-(4-(4-(Diethylaminomethyl)benzoyloxy)phenyl)-2-(3-(2-thienylthio)-8-azabicyclo[3.2.1]oct-8-yl)-1-propanone;

2-(3-Benzyl-3-hydroxy-8-azabicyclo[3.2.1]oct-8-yl-) 1-(4-(4-diethylaminoethyl)benzoyloxy)phenyl)-1-propanone; and 2-(3-Hydroxy-3-phenyl-8-azabicyclo[3.2.1]oct-8-yl)- 1-(4-(4-diethylaminoethyl)benzoyloxy)phenyl)-1-propanone.

EXAMPLE 4

Racemic (1S_*,2S_*)- and
(1R_*,2S_*)-1-(4-Diethylaminomethyl)benzoyloxy)phenyl) -2-(4-hydroxy-4-phenylpiperidino )-1-propanol The title product from the preceding Example was reduced with sodium borohydride as in Example 2. Purification by silica gel chromatography and recrystallization gave first (1S_*,1S_*)-title product (0.28 g, 28%) which had: m.p. 174–175 C (ethanol); NMR (CDCl3) 8.14 (d, J=8.2 Hz, 2H), 7.50 (t, J=8.3 Hz, 4H), 7.43–7.35 (m, 4H), 7.27 (t, J=7.2 Hz, 1H), 7.18 (d, J=8.5 Hz, 2H), 4.31 (d, J=9.7 Hz, 1H), 3.64 (s, 2H), 3.08 (t, J=10.6 Hz, 1H), 2.72–2.60 (m, 4H), 2.53 (q, J=7.1 Hz, 4H), 2.27–2.05 (m, 2H), 1.92 (br s, 1H), 1.82 (br d, J=13.2 Hz, 2H), 1.05 (t, J=7.1 Hz, 6H), 0.87 (d, J=6.6 Hz, 3H); IR (KBr) 3399, 2973, 2947, 1727, 1610, 1271, 1258, 1202, 1078.

Analysis calculated for C$_{32}$H$_{40}$N$_2$O: C, 74.39; H, 7.80; N, 5.42. Found: C, 74.31; H, 7.76; N, 5.38.

The second product isolated was the (1R_*,1S_*)-title product, as its acetate salt (0.119 g, 11%) which had: m.p. 148–150 C (ethanol); NMR (CDCl$_3$) 8.14 (d, J=8.3 Hz, 2H), 7.52–7.27 (m, 10H), 7.18 (d, J=8.6 Hz, 2H), 5.45 (d, J=2.4 Hz, 1H), 3.69 (s, 2H), 3.50 (br d, J=11.6 Hz, 1H), 3.27–3.22 (m, 2H), 3.12–3.03 (m, 2H), 2.57 (q, J=7.1 Hz, 4H), 2.50–2.39 (m, 2H), 2.04 (s, 3H), 1.87 (br t, J=13.6 Hz, 2H), 1.10–1.05 (m, 9H); IR (KBr) 3167, 2967, 2962, 1737, 1257, 1205, 1172, 1071.

Analysis calculated for C$_{32}$H$_{40}$N$_2$O$_4$.C$_2$H$_4$O$_2$: C, 70.81; H, 7.69; N, 4.86. Found: C, 70.72; H, 7.64; N, 4.82.

The HCl salt of the (1S_*,2S_*)-title product recrystallized from ethanol/ether had: m.p. 180–184 C.

Analysis calculated for C$_{32}$H$_{40}$N$_2$O$_4$.2HCl.0.5 H$_2$O: C, 64.20; H, 7.24; N, 4.61. Found: C, 64.02; H, 7.29; N, 4.42.

By the same method the other products of the preceding Example are converted to:

(1S_*,2S_*)- and (1R_*,2S_*)-1-(4-(4-Diethylaminomethyl)benzoyloxy)phenyl)-2-(3-(phenylthio-8-azabicyclo [3.2.1]-oct-8-yl)-1-propanol;

(1S_*,2S_*)- and (1R_*,2S_*)-2-(3-(4-Chlorophenylthio) -8-azabicyclo[3.2.1]oct-8-yl)-1-(4-(4-diethylaminomethyl)benzoyloxy)phenyl-1-propanol;

(1S_*,2S_*)- and (1R_*,2S_*)-1-(4-(4-Diethylaminomethyl)benzoyloxy)phenyl) -2-(2-(thienylthio)-8-azabicyclo[3.2.1]-oct-8-yl)-1-propanol;

(1S_*,2S_*)- and (1R_*,2S_*)-2-(3-Benzyl-3-hydroxy -8-azabicyclo[3.2.1]oct-8-yl)-1-(4-(4-diethylaminoethyl)benzoyloxy)phenyl)-1-propanol; and (1S_*,2S_*)- and (1R_*,2S_*)-2-(3-Hydroxy-3-phenyl -8-azabicyclo[3.2.1]oct-8-yl)-1-(4-(4-diethylaminoethyl)-benzoyloxy)phenyl)-1-propanol.

EXAMPLES 5–10

Substituting an equivalent amount of benzoic acid or of the appropriately substituted benzoic acid for the 4-(morpholinomethyl)benzoic acid, the method of Example 1 was used to prepare the following additional compounds:

5. 2-(4-Hydroxy-4-phenylpiperidino)-1-(4-(4-((1,1-dimethylethyl)aminomethyl)benzoyloxy)phenyl)-1-propanone; m.p. 156 C (hexane trituration, 47% yield).

6. 1-(4-(Benzoyloxy)phenyl)-2-(4-hydroxy-4-phenyl-piperidino )-1-propanone.

7. 2-(4-Hydroxy-4-phenylpiperidino)-1-(4-(4-(piperidinomethyl)benzoyloxy)phenyl)-1-propanone.

8. 2-(4-Hydroxy-4-phenylpiperidino)-1-(4-(4-(2-methylpiperidinomethyl)benzoyloxy)phenyl)-1-propanone.

9. 2-(4-Hydroxy-4-phenylpiperidino)-1-(4-(4-(dimethylaminomethyl)benzoyloxy)phenyl-1-propanone.

10. 1-(4-(3-(Diethylaminomethyl)benzoyloxy)phenyl)-2-(4-hydroxy-4-phenylpiperidino )-1-propanone.

EXAMPLE 11

Racemic (1S_*,
2S_*)-2-(4-Hydroxy-4-phenylpiperidino)-
1-(4-(4-((1,1-dimethylethyl)aminomethyl)benzoyloxy)phenyl)-1-propanol Lithium aluminum hydride (0.08 g, 2.11 mmol) was slurried in dry tetrahydrofuran (12 mL) and chilled to –78 C. The ketone product of Example 5 (0.44 g, 0.86 mmol) was added neat all at once to this cold slurry followed by continued stirring at –78 C for 1 hour. The mixture which had now become a gel was diluted with tetrahydrofuran (10 mL) and quenched with acetic acid (0.48 mL, 8.4 mmol). The solvent was removed at reduced pressure and the residue was flash chromatographed on silica gel (1×6 inches, packed in 30% ethyl acetate/hexane). Ethyl acetate/hexane gradient elution gave no product. Continued elution with 10% methanol/ethyl acetate yielded the product as an actate salt. This solid was suspended in ethyl acetate and vigorously shaken with saturated sodium bicarbonate. The phases were separated and the aqueous layer was extracted twice with ethyl acetate. The combined organic layer was dried over calcium sulfate and concentrated. The residue was recrystallized from methanol to afford 30 mg (6.7%) of the title product as a white solid; m.p. 195–197 C; NMR (CDCl$_3$) 8.15 (d, J=8.5 Hz, 2H), 7.53 (t, J=7 Hz, 4H), 7.48–7.24 (m, 5H), 7.20 (d, J=8.5 Hz, 2H), 4.34 (d, J=9.5 Hz, 1H), 3.85 (s, 2H), 3.13 (long range coupled t, J=10.5 Hz, 1H), 2.86–2.61 (m, 4H), 2.38–2.09 (sym m, 2H), 1.88 (br d, J=13.5 Hz, 2H), 1.38 (small impurity), 1.26 (s, 1H), 0.90 (d, J=6.5 Hz, 3H). One hydroxyl proton was not observed.

Analysis calculated for $C_{32}H_{40}N_2O_4$: C, 74.39; H, 7.80; N, 5.42. Found: C, 73.98; H, 7.80; N, 5.18.

EXAMPLES 12–16

Using the ketone reduction procedures of the prior Examples, the ketones of Examples 6–10 were converted to the following racemic compounds:

12a. (1S_*,2S_*)-1-(4-(Benzoyloxy)phenyl)-2-(4-hydroxy-4-phenylpiperidino)-1-propanol; 38% yield; m.p. 166 C (from ethanol). 12b (1R_*,2S_*)-1-(4-(Benzoyloxy)phenyl) -2-(4-hydroxy-4-phenylpiperidino)-1-propanol; 17% yield; m.p. 188–191 C (from ethanol).

13a. (1S*,2S*)-2-(4-Hydroxy-4-phenylpiperidino) -1-(4-(4-(piperidinomethyl)benzoyloxy)phenyl)-1-propanol; 29% yield; m.p. 175 C (dec), (from ethyl acetate).

13b. (1R_*,2S_*)-2-(4-Hydroxy-4-phenylpiperidino) -1-(4-(4-(piperidinomethyl)benzoyloxy)phenyl)-1-propanol; 15% yield; m.p. 167 C (dec), (from ethyl acetate).

14a. (1S_*,2S_*)-2-(4-Hydroxy-4-phenylpiperidino) -1-(4-(4-(2-methylpiperidinomethyl)benzoyloxy)phenyl)-1-propanol; 37% yield; m.p. 179 C (dec), (from ethyl acetate).

14b. (1R_*,2S_*)-2-(4-Hydroxy-4-phenylpiperidino) -1-(4-(4-(2-methylpiperidinomethyl)benzoyloxy)phenyl)-1-propanol; 16% yield; m.p. 160 C (dec), (from ethyl acetate).

15a. (1S_*,2S_*)-2-(4-Hydroxy-4-phenylpiperidino) -1-(4-(4-(2-dimethylaminomethyl)benzoyloxy)phenyl)-1-propanol; 7% yield; m.p. 195–198 C (dec), (from methanol).

15b. (1R_*,2S_*)-2-(4-Hydroxy-4-phenylpiperidino) -1-(4-(4-(2-dimethylaminomethyl)benzoyloxy)phenyl)-1-propanol; 26% yield; m.p. 162–182 C (dec), (from ethyl acetate).

16. (1S_*,2S_*)-1-(4-(3-(Diethylaminomethyl)benzoyloxy)phenyl) -2-(4-hydroxy-4-phenylpiperidino)-1-propanol; 14% yield; m.p. 119–123 C (from methylcyclohexane).

EXAMPLE 17

Racemic (1S_*,2S_*)-1-(4-(4-(Diethylaminomethyl)benzoyloxy)phenyl)-2-(4-hydroxy -4-phenylpiperidino)-1-propanol Carbonyl diimidizole (0.25 g, 1.54 mmol) and racemic (1S_*,2S_*)-1-(4-hydroxyphenyl)-2-(4-hydroxy-4-phenylpiperidino)-1-propanol hydrochloride (0.37 g, 1.52 mmol; Chenard, International Patent Application Publication No. WO 90/14088, Example 38 at page 42) in dry CH$_2$Cl$_2$ (10 ml) were stirred for 1 hour at ambient temperature. 4-(Diethylaminomethyl)benzoic acid (0.50 g, 1.53 mmol) was then added and the resulting mixture was stirred overnight. The reaction mixture was then washed with saturated NaHCO$_3$, H$_2$O and brine, dried with MgSO$_4$ and concentrated to give a white solid (0.41 g) which $^1$HNMR (CDCl$_3$) showed to be a mixture of the acid, desired monoester and undesired diesterified material. Purification by silica gel flash chromatography (1×6 inches, ethyl acetate/hexane gradient for elution) gave 100 mg of crude title product as a colorless oil. This material was recrystallized from ethanol to yield purified title product (33 mg, 4.2%) having properties identical with those of the the (1S_*, 2S_*)-title product of Example 4.

By the same method, the enantiomeric (1S_,2S_)- and (1R_,2R_)-1-(4-hydroxyphenyl)-2-(4-hydroxy-4-phenylpiperidino)-1-propanols (WO 90/14088, Example 78 at page 47) are converted to the corresponding 4-(diethylaminomethyl)benzoate esters.

PREPARATION 1-(4-Hydroxyphenyl)-2-(4-hydroxy-4-phenylpiperidino)-1-propanone 1-(4-(Triisopropylsilyloxy)phenyl)-2-(4-hydroxy-4-phenylpiperidino)-1-propanone (International Application Publication Number: WO 90/14088, Example 36 at page 41; 22.0 g, 45.7 mmol) was dissolved in dry tetrahydrofuran (500 mL). Tetrabutylammonium fluoride (55 ml, 55 mmol, 1N in tetrahydrofuran) was added dropwise to the stirred solution over 3 minutes. After stirring for 1 hour, the reaction mixture was concentrated and the concentrate flash chromatographed on silica gel (3×6 inches). The column was gradiently eluted with ethyl acetate/hexane, then sequentially with 100% ethyl acetate, 1:9 methanol:ethyl acetate and finally with 1:5 methanol:ethyl acetate. Product-containing fractions were stripped to yield 16.7 g (100%) of title product as a light yellow solid which was triturated with hexane; m.p. 95–97 C; $^1$H-NMR (CDCl$_3$) delta (ppm) 8.08 (d, J=8.5 Hz, 2H), 7.48 (d, J=8 Hz, 2H), 7.34 (t, J=8 Hz, 2H), 7.28–7.25 (m, 1H partially obscured by CHCl$_3$ from NMR solvent), 6.89 (d, J=8.5 Hz, 2H), 4.15 (q, J=7 Hz, 1H), 3.0–2.65 (m, 4H), 2.25–2.10 (m, 2H), 1.85–1.77 (m, 2H), 1.35 (d, J=7 Hz, 3H).

By the same method, other triisopropylsilyl protected ketones of said WO 90/14088 were converted to unprotected ketones as follows:

2-(4-Benzyl-4-hydroxypiperidino)-1-(4-hydroxy-phenyl)-1-propanone;

2-(4-(4-Chlorophenyl)-4-(hydroxypiperidino)-1-(4-hydroxyphenyl)-1-propanone;

1-(4-Hydroxyphenyl)-2-(3-(phenylthio)-8-azabicyclo [3.2.1]oct-8-yl)-1-propanone;

2-(3-(4-Chlorophenylthio)-8-azabicyclo[3.2.1]oct-8-yl)-1-(4-hydroxyphenyl)-1-propanone;

1-(4-Hydroxyphenyl)-2-(3-(2-thienylthio)-8-azabicyclo [3.2.1]oct-8-yl)-1-propanone;

2-(3-Benzyl-3-hydroxy-8-azabicyclo[3.2.1]oct-8-yl) -1-(4-hydroxyphenyl)-1-propanone; and 1-(4-Hydroxyphenyl)-2-(3-hydroxy-3-phenyl-8-azabicyclo [3.2.1]oct-8-yl)-1-propanone.

I claim:

1. A method for treating spinal cord trauma in a mammal in need of such treatment comprising administering to said mammal an effective NMDA blocking amount of a compound of the formula

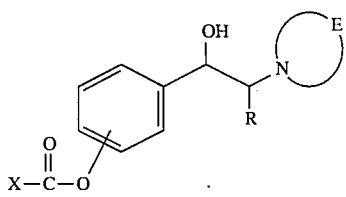

wherein

E is

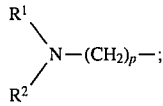

R is H, $(C_1-C_6)$alkyl, $(C_2-C_6)$alkenyl or $(C_2-C_6)$alkynyl;

X is phenyl, benzyl, $(C_1-C_3)$alkoxy, phenoxy or one of said groups substituted on aromatic carbon by

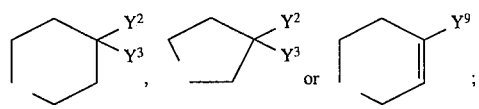

p is 1 or 2;

$R^1$ and $R^2$ are taken separately and are each independently hydrogen or $(C_1-C_6)$ alkyl, or $R^1$ and $R^2$ are taken together with the nitrogen to which they are attached to form a pyrrolidine, piperidine or morpholine ring, or one of said rings substituted by $(C_1-C_3)$alkyl;

$Y^2$ and $Y^3$ are taken together and are

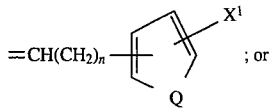 ; or $Y^2$ and $Y^3$ are taken separately, and $Y^1$ is OH and $Y^3$ is

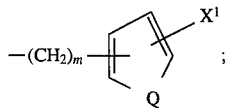 ;

$Y^9$ is

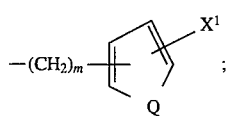 ;

n is 0, 1, 2 or 3;

m is 0, 1, 2, 3 or 4;

Q is S or CH=CH; and $X^1$ is hydrogen, $(C_1-C_3)$alkyl, $(C_1-C_3)$alkoxy or halo;

or a pharmaceutically acceptable acid addition salt thereof.

* * * * *

UNITED STATES PATENT AND TRADEMARK OFFICE
CERTIFICATE OF CORRECTION

PATENT NO. : 5,594,007
DATED : January 14, 1997
INVENTOR(S) : Bertrand L. Chenard It is certified that error appears in the above-identified patent and that said Letters Patent is hereby corrected as shown below:

Column 3, line 47 - "wherein" should read -- wherein E is --

Column 3, line 62, "5p is 1 or 2;" should read -- p is 1 or 2 --.

Column 5, line 55, "carded" should read -- carried --.

Column 6, line 58, "95:50" should read -- 95:5 --.

Signed and Sealed this

Fourteenth Day of October, 1997

Attest:

BRUCE LEHMAN

Attesting Officer

Commissioner of Patents and Trademarks